United States Patent
Richardson et al.

(10) Patent No.: US 10,010,749 B2
(45) Date of Patent: Jul. 3, 2018

(54) THORACIC STABILIZER

(71) Applicant: GRAVITY FITNESS AUSTRALIA PTY LTD, Brisbane, Queensland (AU)

(72) Inventors: David Alexander Richardson, Brisbane (AU); Carolyn Anne Richardson, Brisbane (AU)

(73) Assignees: Carolyn Anne Richardson, Brisbane (AU); David Alexander Richardson, Brisbane (AU); Gravity Fitness Australia Pty Ltd, Brisbane (AU)

( * ) Notice: Subject to any disclaimer, the term of this patent is extended or adjusted under 35 U.S.C. 154(b) by 0 days.

(21) Appl. No.: 14/422,067

(22) PCT Filed: Aug. 19, 2013

(86) PCT No.: PCT/AU2013/000919
§ 371 (c)(1),
(2) Date: Feb. 17, 2015

(87) PCT Pub. No.: WO2014/026249
PCT Pub. Date: Feb. 20, 2014

(65) Prior Publication Data
US 2015/0217162 A1  Aug. 6, 2015

(30) Foreign Application Priority Data
Aug. 17, 2012 (AU) .................. 2012903573

(51) Int. Cl.
*A63B 23/02* (2006.01)
*A63B 71/06* (2006.01)
(Continued)

(52) U.S. Cl.
CPC ...... *A63B 23/0244* (2013.01); *A63B 21/0552* (2013.01); *A63B 21/0557* (2013.01);
(Continued)

(58) Field of Classification Search
CPC ............ A63B 23/0244; A63B 23/0238; A63B 23/1236; A63B 23/0405; A63B 21/4025;
(Continued)

(56) References Cited

U.S. PATENT DOCUMENTS

| | | | | |
|---|---|---|---|---|
| 1,402,179 A | * | 1/1922 | Piscitelli | A63B 21/0004 482/124 |
| 2,280,274 A | * | 4/1942 | Wildermuth | A61H 1/008 482/131 |

(Continued)

FOREIGN PATENT DOCUMENTS

| WO | WO-2007134380 A1 | 11/2007 |
|---|---|---|
| WO | WO-2012016292 A1 | 2/2012 |

OTHER PUBLICATIONS

International Search Report for PCT/AU2013/000919, dated Dec. 4, 2013; ISA/AU.

*Primary Examiner* — Loan H Thanh
*Assistant Examiner* — Megan Anderson
(74) *Attorney, Agent, or Firm* — Harness, Dickey & Pierce, P.L.C.

(57) ABSTRACT

The invention provides an exercise device for strengthening muscles in the scapula-thoracic region. The device enables simulated weight-bearing action for the upper limb while maintaining good postural form. The device can also be used to provide feedback on good postural form. The exercise device comprises a spine contact member (26) to be positioned at the thoracic curve of a person (10), and two rigid planar members (28) which extend laterally from the spine contact member (26). The rigid planar members (28) are positioned over the scapulae of the person (10). The spine contact member (26) and associated rigid planar members (28) are held in position by straps (30) which pass over and under the shoulders of the person (10).

20 Claims, 7 Drawing Sheets (51) Int. Cl.
*A63B 21/055* (2006.01)
*A63B 24/00* (2006.01)
*A63B 21/00* (2006.01)
*A61H 23/02* (2006.01)
*A63B 23/04* (2006.01)
*A63B 23/12* (2006.01)
*A61N 1/05* (2006.01)
*A61N 1/36* (2006.01)

(52) U.S. Cl.
CPC ...... *A63B 21/4005* (2015.10); *A63B 21/4007* (2015.10); *A63B 21/4025* (2015.10); *A63B 21/4035* (2015.10); *A63B 21/4039* (2015.10); *A63B 23/0238* (2013.01); *A63B 24/0062* (2013.01); *A63B 71/06* (2013.01); *A61H 23/02* (2013.01); *A61H 2201/10* (2013.01); *A61H 2201/1614* (2013.01); *A61H 2201/1652* (2013.01); *A61H 2201/1695* (2013.01); *A61H 2205/081* (2013.01); *A61N 1/0551* (2013.01); *A61N 1/3605* (2013.01); *A63B 23/0405* (2013.01); *A63B 23/1236* (2013.01); *A63B 2071/0602* (2013.01); *A63B 2071/0655* (2013.01); *A63B 2220/56* (2013.01); *A63B 2225/50* (2013.01)

(58) Field of Classification Search
CPC ............ A63B 21/4007; A63B 21/4005; A63B 21/4035; A63B 21/4039; A63B 21/0557; A63B 21/0552; A63B 24/0062
USPC .................................................... 482/1, 4, 8
See application file for complete search history.

(56) References Cited

U.S. PATENT DOCUMENTS

| | | | |
|---|---|---|---|
| 4,653,750 A | 3/1987 | McIntyre | |
| 4,934,005 A * | 6/1990 | Martin | A47C 16/00 5/652 |
| 4,961,573 A * | 10/1990 | Wehrell | A63B 21/0552 482/124 |
| 5,113,176 A * | 5/1992 | Harris | A47C 7/425 340/573.7 |
| 5,143,088 A * | 9/1992 | Marras | A61B 5/103 33/512 |
| 5,509,873 A * | 4/1996 | Corn | A63B 21/153 482/124 |
| 5,769,764 A | 6/1998 | Tilberis | |
| 5,921,903 A * | 7/1999 | Lawrence | A63B 23/0211 482/131 |
| 6,663,546 B2 * | 12/2003 | Kallassy | A63B 23/0211 482/139 |
| 7,141,012 B2 * | 11/2006 | Lin | A63B 21/0004 482/121 |
| 8,088,084 B2 * | 1/2012 | Zahos | A61N 7/02 600/437 |
| 2006/0113343 A1 * | 6/2006 | Chang | A63B 55/408 224/576 |
| 2008/0200853 A1 * | 8/2008 | Tielve | A61H 1/0292 601/134 |
| 2009/0177121 A1 * | 7/2009 | Brandon | A61B 5/103 600/587 |
| 2010/0088803 A1 * | 4/2010 | Orloff | A41D 13/0015 2/228 |

* cited by examiner

THORACIC STABILIZER

CROSS REFERENCE TO RELATED APPLICATIONS

This application is a U.S. National Phase Application under 35 U.S.C. 371 of International Application No. PCT/AU2013/000919 filed on Aug. 19, 2013 and published as WO 2014/026249 A1 on Feb. 20, 2014. This application is based on and claims the benefit of priority from Australian Patent Application No. 2012903573 filed Aug. 17, 2012. The entire disclosures of all of the above applications are incorporated herein by reference.

TECHNICAL FIELD

The present invention relates to a device for strengthening muscles in the scapula-thoracic region.

BACKGROUND ART

The reference to any prior art in this specification is not, and should not be taken as an acknowledgement or any form of suggestion that the prior art forms part of the common general knowledge.

The spine is a complex, flexible structure which can change its shape and move in all directions. It consists of vertebrae, intervertebral discs, and intervertebral joints (which are attached to ribs in the thoracic area) which house the spinal cord and the nerves leading out to the body. Protection of this complex and vulnerable structure during sustained or heavy loading which involves the spine can only be achieved by appropriate muscle function which serves to hold the spine in its 'neutral' position.

The neutral spine, which is formed by three spinal curves (cervical, thoracic and lumbo-sacral curves), is usually described as the 'S' shape, neutral spine position. The curves are formed by the shape of the vertebrae and the intervertebral discs, and, most importantly, by muscles which hold the shape of the three curves. The three curves allow the spine to act as a spring to withstand stress and negate impact loads caused by the vertical force of gravity. The individual curves making up the neutral spine position lie each side of the vertical line of good posture, that is, the imaginary line, viewed from the side, through the mastoid process, centre of the shoulder joint and the centre of the hip joint. Descriptions of the individual curves are as follows:
  (i) curve of the neck region—the concave cervical spinal curve lies in front of the vertical line and is closely linked to the position of the head;
  (ii) curve of the low back—the concave lumbo-sacral spinal curve also lies in front of the vertical line, and is closely linked to movement of the pelvis and lower limb; and
  (iii) curve of the thorax (ribs attached)—in contrast to the neck and low back regions, the convex thoracic curve lies behind the vertical line of good posture.

The convex thoracic curve is closely linked to movement and position of the scapula and associated upper limb. To hold the thoracic curve firm, the scapulo-thoracic muscles (mainly serratus anterior) must produce a backwardly directed muscle force on the spine whilst also causing the scapula to become flat against the chest wall. This action can only be produced with concomitant activation and strengthening of the scapulo-thoracic muscles (mainly serratus anterior) through weight-bearing exercise for the upper limb [see the 'weightbearing' test for serratus anterior described in Kendall et al. 'Muscles: Testing and Function, with. Posture and Pain', Lippincott Williams & Wilkins, 2005]. In a healthy spine with scapulo-thoracic muscles (mainly serratus anterior) working correctly, the thoracic spine retains its curve, and the scapula is held flat against the rib cage.

The complex structure of the spine is protected and managed through a specialised deep muscle system which supports and holds the three individual curves of the neutral spine. Serratus anterior muscle forms an important part of this deep muscle system. Maintenance of the neutral spine position is important when the spine is dealing with sustained or heavy loading and importantly, to provide a firm central axis for axial rotation (twisting) activities of the spine. Activities where maintenance of a neutral spine is important include the following:
  (i) walking (low loading for the spine), where the neutral spine is held firm and supported for sustained periods in a upright position and gives the classic 'good postural form';
  (ii) prolonged leaning forward activities requiring increased sustained loading (as required by certain occupations, for example, dentist or factory worker) where the spine requires strong muscles to support it in the neutral spine position;
  (iii) sports such as golf, cricket and tennis which involve trunk twisting, where the spine requires short periods of using even stronger spinal muscles to allow the neutral spine position to form a strong central axis for trunk rotation (in the lean forward position); and
  (iv) lifting, as safe lifting techniques depend on maintaining a strong neutral spine position. In particular, when lifting very heavy loads, the spine requires even stronger spinal muscles to maintain the neutral spine position in a lean forward position which is often accompanied by twisting movements.

As a result of more sedentary modern lifestyles and robotic technology, people are developing poor spinal postures. In other words, people's spines are weakening and they are losing the ability to hold the upright neutral spine position. Weakness of the muscles controlling the spinal curves is also a result of lack of weight-bearing exercise for the upper limbs. Consequently, spinal structures are becoming far more vulnerable to injury, increasing spinal pain, disc injury and referred pain, osteoarthritis and other painful joint problems of the shoulder and hip.

General weakness of the spine is demonstrated with a loss of the normal, natural spinal curves each side of the vertical line of good posture. Loss of the natural spinal curves can take many forms, but during exercise it mostly results in the spine having a 'C' shaped curve or a reversed 'C' shape. Exercise with the spine in either of these positions will weaken, rather than strengthen, the spine.

Thus the neutral spine position is considered important for our musculo-skeletal health as, in this position, the muscles are capable of supporting and protecting the spine from injury. It is particularly the activation and strengthening of muscles that maintain the thoracic curve that has not been addressed in exercises currently used to strengthen the neutral spine.

Figure 4:
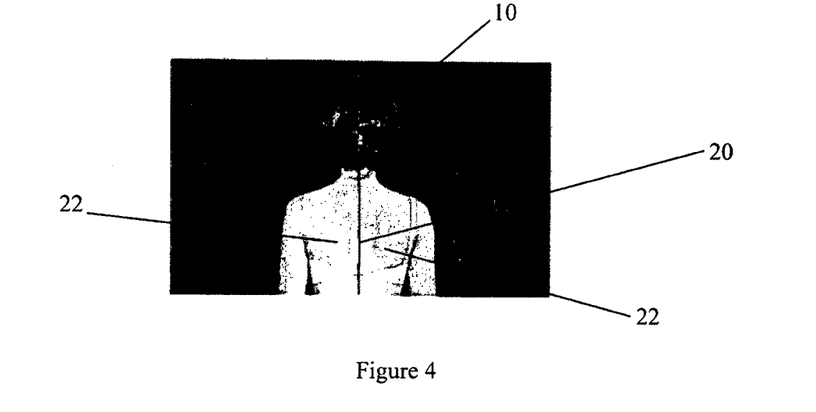
FIG. 4 is a photograph of a person demonstrating a flattened thoracic curve and protruding scapula.

Specifically for the thoracic curve, weakness of the serratus anterior muscle when standing upright is demonstrated by a flattened thoracic curve and 'winging' of the scapula, where the medial border of the scapula lifts away from the chest wall and protrudes far more posteriorly than the thoracic spine (see FIG. 4).

The serratus anterior muscle lies very deep under the large bone of the scapula, so facilitation techniques normally used to activate and train superficial muscles cannot be used. In addition, because the serratus anterior lies under bone, it cannot be viewed, facilitated or strengthened using real-time ultrasound imaging techniques (which are used as feedback techniques).

To ensure the stability and strength of the scapula-thoracic region, a specific type of strengthening exercise is required. This consists of an upper limb weight-bearing exercise, with axial (weight-bearing) resistance providing axial-compression longitudinally through the whole upper limb, as well as producing a backwardly directed muscle force to strengthen the curve of the thoracic spine. It is important when performing upper limb weight-bearing exercise that correct postural form is maintained in order to maintain the correct position of the thoracic curve.

There thus exists a need for a new feedback exercise device, to assist in strengthening weak muscles of the scapula-thoracic region as well as help monitor and maintain good posture. Such a device necessarily needs to specifically strengthen the serratus anterior in its weight-bearing role of displacing the thorax posteriorly and holding the scapula flat against the chest wall. This type of exercise would strengthen the thoracic curve and in turn strengthen the whole neutral spine position.

International Patent Publication, WO 2007/134380, describes a feedback device used to monitor the position of the lumbo-sacral curve and ensure the correct muscles are working. Feedback exercise tools are particularly important as they give feedback to a person as to whether or not the three spinal curves are being maintained and therefore whether or not the deep muscles supporting them are being exercised.

It would be desirable to have a feedback exercise device that allows the user to feel the position of the thoracic spine and the position of the scapula in relation to the thoracic spine. The user of such an exercise device could therefore undertake upper limb weight-bearing exercise to strengthen the scapulo-thoracic muscles (mainly serratus anterior) whilst maintaining correct postural form and thus properly maintaining the curve of the thoracic spine. Such an exercise device could also be used to maintain correct postural form and thus the correct position of the thoracic curve, during daily activities or when sitting for prolonged periods.

Despite a need for a feedback exercise device that allows the user to feel the position of the thoracic spine and the position of the scapula in relation to the thoracic spine and thus provides feedback as to correct postural form and maintenance of the thoracic curve, such a device has not been provided.

SUMMARY OF INVENTION

With the foregoing in view, the present invention in one form, resides broadly in an exercise device comprising:
(i) sensory means comprising a spine contact member and two rigid planar members extending laterally from the spine contact member; and
(ii) an adjustable strap system for securing the sensory means to a wearer of said exercise device;
such that in use, the spine contact member is positioned on the thoracic curve of the wearer and each rigid planar member is positioned over a scapula of the wearer.

The spine contact member can be any suitable shape that will contact the thoracic curve of a wearer when the exercise device is in use. Preferably, the spine contact member protrudes from the plane of the two rigid planar members. Even more preferably, the spine contact member is a convex structure. The spine contact member can thus press onto the thoracic curve of a wearer and provide tactile feedback.

The spine contact member can protrude from the plane of the two rigid planar members by any suitable height. In a preferred embodiment, the spine contact member protrudes from the plane of the two rigid planar members by a distance of approximately 1.5 cm to 2 cm. The actual distance the spine contact member protrudes can vary dependent on the size and shape of the user of the exercise device.

The spine contact member can have a smooth surface that contacts the thoracic curve of a wearer. Alternatively, the spine contact member can have one or more projections on the surface that contacts the thoracic curve of a wearer. The projections can be in the form of spikes, bumps or other such protrusions such that during use of the exercise device, at least one of the projections is in contact with the thoracic curve of the wearer.

The spine contact member can further comprise means for providing stimulation to the point of contact on the thoracic curve of the spine contact member. The stimulation can be in the form of electrical stimulation or vibratory stimulation.

The two rigid planar members extend laterally from the spine contact member, such that when the spine contact member is positioned on the thoracic curve of a wearer, each rigid planar member is positioned over a scapula of the wearer. The rigid planar members can be made of any suitable material. Preferably, for ease of manufacture and to minimise the weight of the device, the rigid planar members are made from a hard plastic.

The two rigid planar members can each have a smooth surface that is in proximity to the scapulae of a wearer. Alternatively, the two rigid planar members can have one or more projections on the surface that is in proximity to the scapulae of a wearer. The projections can be in the form of spikes, bumps or other such protrusions such that during use of the exercise device, at least one projection from each rigid planar member is in contact with a scapula of the wearer.

The two rigid planar members can further comprise means for providing stimulation to the point of contact on the scapulae. The stimulation can be in the form of electrical stimulation or vibratory stimulation.

The sensory means can further comprise at least one pressure sensor. The pressure sensor can be associated with the spinal contact member, or a pressure sensor can be associated with each rigid planar member. In a further alternative, the sensory means can comprise three pressure sensors, one associated with the spinal contact member, and one associated with each rigid planar member. Each pressure sensor can provide feedback to a monitoring device, thus providing feedback on posture during exercise or for posture awareness during daily activities. Each pressure sensor can be connected to a monitoring device by suitable means known in the art.

Each pressure sensor can be any suitable type of pressure sensor. Preferably, each pressure sensor is an electronic pressure sensor. Even more preferably, the electronic pressure sensor uses a force collector to sense pressure. It is particularly preferred that feedback from an electronic pressure sensor is transmitted wirelessly to a monitoring device.

In certain embodiments, the sensory means comprising a spine contact member and two rigid planar members extending laterally from the spine contact member can be of a unitary construction. For example, the spine contact member and rigid planar members can be integrally moulded. In alternative embodiments, the spine contact member and rigid planar members can be separate components connectable by any suitable means, such as by locking lugs.

In certain embodiments where the sensory means is of a unitary construction, the spine contact member can be exchangeable, such that the spine contact member can be readily exchanged for a different type of spine contact member. For example, exchanging a smooth spine contact member for a spine contact member with projections. Other variations include interchangeable spine contact members having different heights relative to the plane of the two rigid planar members.

In embodiments where the spine contact member and rigid planar members are separate components, the spine contact member can be readily exchanged for a different type of spine contact member. For example, exchanging a smooth spine contact member for a spine contact member with projections. Other variations include interchangeable spine contact members having different heights relative to the plane of the two rigid planar members.

The adjustable strap system can be any suitable combination of straps that will hold the sensory means in position on a wearer of the exercise device. Providing a strap system that is adjustable enables the exercise device to be worn by a range of differently sized people. The strap system can also be adjusted to accommodate different weight-bearing exercises which may require more or less movement of the wearer.

Preferably the adjustable strap system comprises at least one flexible, extensible strap. The at least one flexible, extensible strap can be made from any suitable material such as a rubberized strip of material. Particularly preferred is the material commonly used in the exercise industry for elastic resistant bands or elastic resistant straps.

The adjustable strap system preferably comprises straps adapted to fit over the shoulders and under the arms of a wearer, in the form of a harness. A strap system that fits around the arms of a wearer in this way, enables the sensory means to be positioned such that the spine contact member is in contact with the thoracic curve of the wearer and each rigid planar member is positioned over a scapula of the wearer.

The adjustable strap system can comprise any suitable adjustment means. The strap system can thus comprise one or more buckles. Alternatively, the adjustment means can comprise one or more clip devices or tensioners which allow the length of a strap to be adjusted.

The adjustable strap system can further comprise handles or hand-grips for the wearer to hold during simulated weight-bearing exercises. The handles or hand-grips can be removably attached to the straps that fit over the shoulders and under the arms of the wearer. In an alternative embodiment, the handles or hand-grips can simply be extensions of or attachments to the straps that fit over the shoulders and under the arms of the wearer.

In a particularly preferred embodiment of the invention, the adjustable strap system comprises a single continuous elastic band of sufficient length to extend from the sensory means, over and under each shoulder of a wearer of the exercise device, and provide handles or hand-grips at the front of the wearer.

Any of the features described herein can be combined in any combination with any one or more of the other features described herein within the scope of the invention.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of Invention in any way. The Detailed Description will make reference to a number of drawings as follows:

FIG. 11 is a side view of a person wearing an exercise device of the invention, illustrating the directions that pushing exercises can be undertaken in;

DETAILED DESCRIPTION OF EMBODIMENTS

Figure 1:
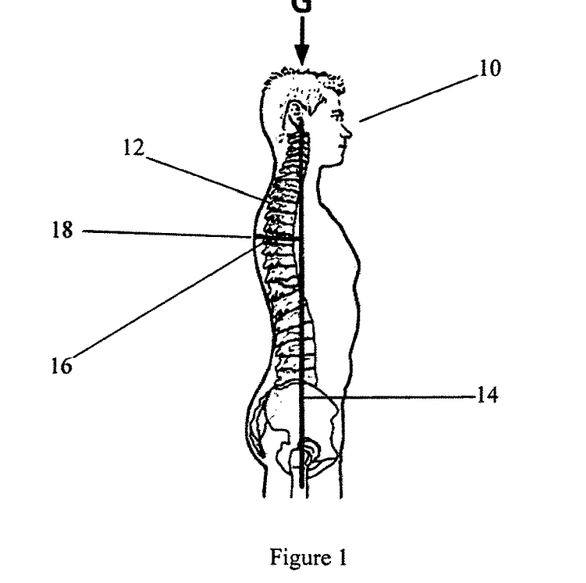
FIG. 1 is a side view of a person showing a neutral spine.

In FIG. 1, there is shown a side view of a person 10 with a neutral spine 12. The imaginary, vertical line of good posture 14 through the mastoid process, centre of the shoulder joint and the centre of the hip joint is indicated, as is the distance 16 between the apex of the thoracic curve 18 (approximately T5-T7) and the vertical line of good posture 14.

Figure 2:
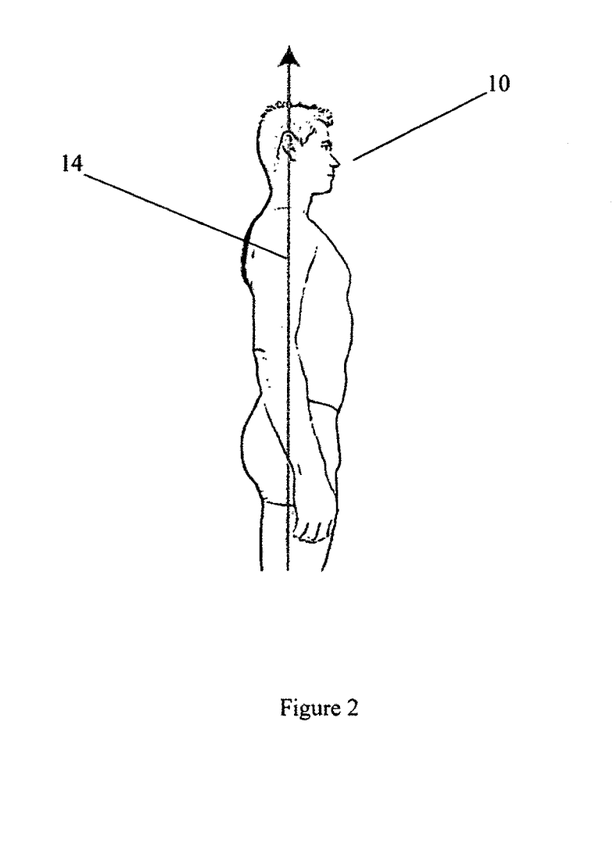
FIG. 2 is a side view of a person with a healthy spine demonstrating good posture.

In FIG. 2, a side view of a person 10 demonstrating good posture with the curved shape of the thoracic spine and the scapula held flat against the rib cage is shown. To adopt good posture in this manner requires working the scapulo-thoracic muscles (mainly serratus anterior) to maintain the thoracic spine curve, as well as holding the scapula flat against the rib cage.

Figure 3:
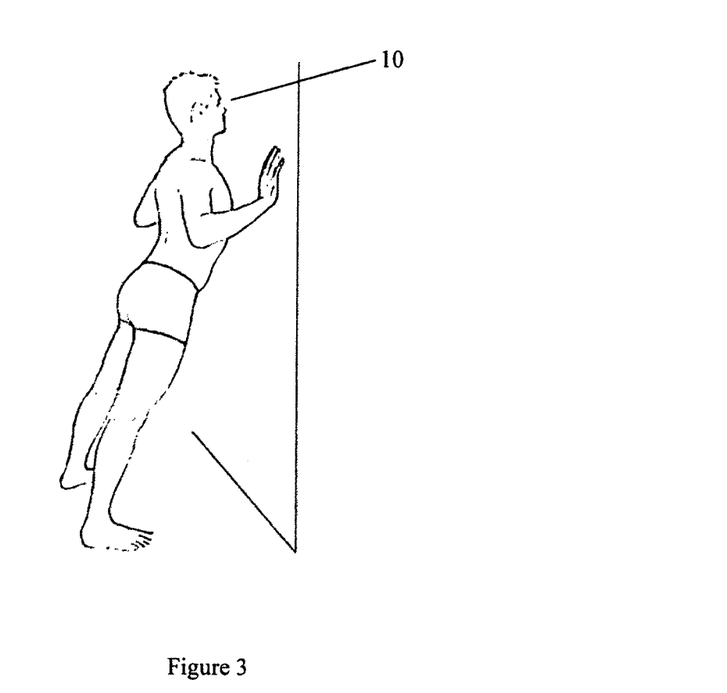
FIG. 3 is an image of a person whose spine has lost its neutral shape.

In FIG. 3, the person 10 is attempting 'wall push ups' as a strengthening exercise, but has lost the neutral shape of their spine. Instead, the spine has moved into a reversed 'C' shape. Continued exercise with the spine in this position will weaken rather than strengthen the spine.

The image in FIG. 4 shows a person 10 with a flattened thoracic curve 20 and scapula 22 which are lifted away from the chest wall and protruding more posteriorly than the thoracic curve of the spine. This is known as 'winging' of the scapula.

Figure 5:
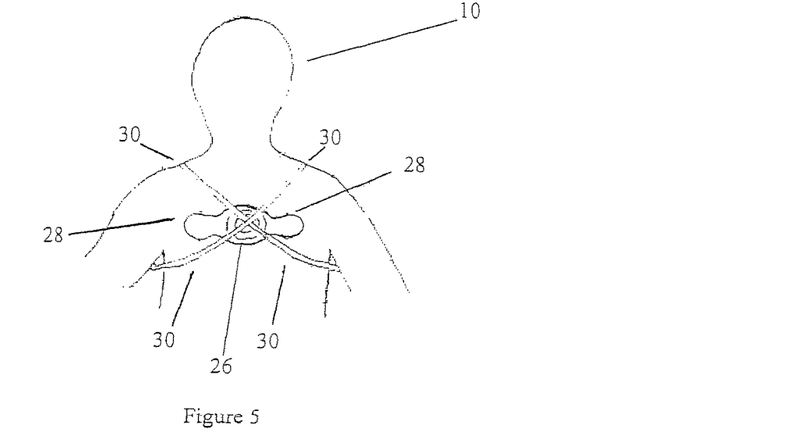
FIG. 5 shows a rear view of a person wearing an exercise device according to one embodiment of the invention.

FIG. 5 shows a rear view of a person 10 wearing an exercise device according to one embodiment of the invention. The device comprises a spine contact member 26 positioned at the thoracic curve of the person 10, and two rigid planar members 28 which extend laterally from the spine contact member 26. The rigid planar members 28 are positioned over the scapula of the person 10. The spine contact member 26 and associated rigid planar members 28 are held in position by straps 30 which pass over and under the shoulders of the person 10.

Figure 6:
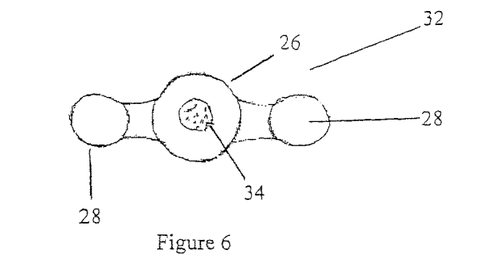
FIG. 6 is a view of the underside of the sensory means of the exercise device of FIG. 5.

The underside of the sensory means 32 of an exercise device is shown in FIG. 6. The underside is the side that is in contact with a wearer 10 when the device is in use. In this embodiment, the spine contact member 26 has a series of rubber protrusions 34, which in situ press into the surface of the thoracic curve and provide tactile feedback.

Figure 6A:
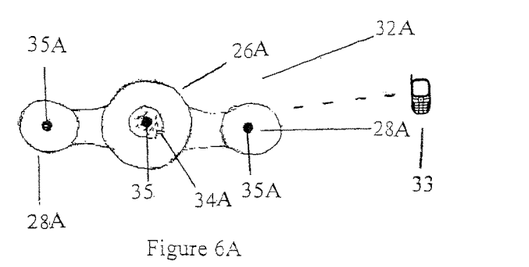
FIG. 6A is a view of the underside of an alternative embodiment of the sensory means of the exercise device of FIG. 5.

The underside of a sensory means 32A of an alternative embodiment of the exercise device of FIG. 5 is shown in FIG. 6A. In this embodiment, the spine contact member 26A also has a series of rubber protrusions 34A, which in situ press into the surface of the thoracic curve and provide tactile feedback. Additionally, in this embodiment, the spine contact member 26A has a pressure sensor 35 on the spine contact member 26A and a pressure sensor 35A on each rigid planar member 28A.

In the particular embodiment shown in FIG. 6A, the pressure sensors 35, 35A are in wireless communication with a pressure monitoring device 33. Typically, the pressure monitoring device is a smart phone, tablet or similar.

Figure 7:
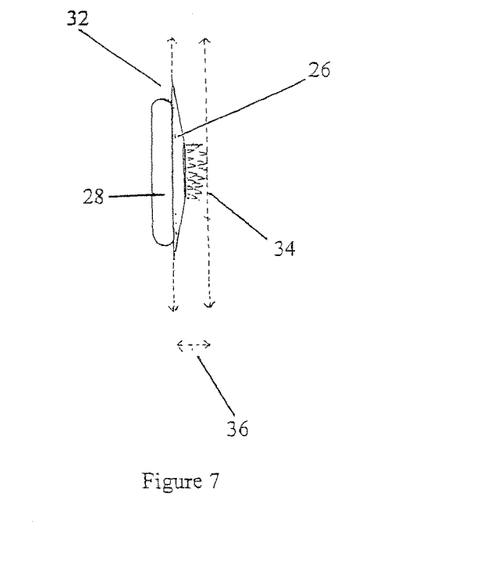
FIG. 7 is a side view of the spine contact member of the exercise device of FIG. 5.

A side view of the sensory means 32 of an exercise device is shown in FIG. 7. The spine contact member 26 has a series of protrusions 34 which in situ press into the surface of the thoracic curve and provide tactile feedback. The spine contact member 26 thus has a height 36 of approximately 1.5 cm to 2 cm above the plane of the rigid planar members 28.

Figure 8:
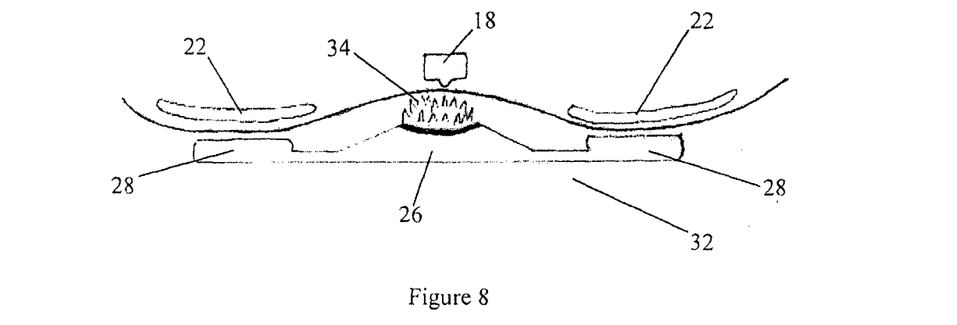
FIG. 8 is a cross-sectional view of the sensory means of an exercise device according to an embodiment of the invention illustrating good posture.

A cross-sectional view of the sensory means 32 of an exercise device illustrating correct position in good posture is shown in FIG. 8. The position of the apex of the thoracic spine 18 can be felt by the wearer through the spine contact member 26 and associated protrusions 34. In addition, the rigid planar members 28 can be felt on top of the shoulder blades 22.

Figure 9:
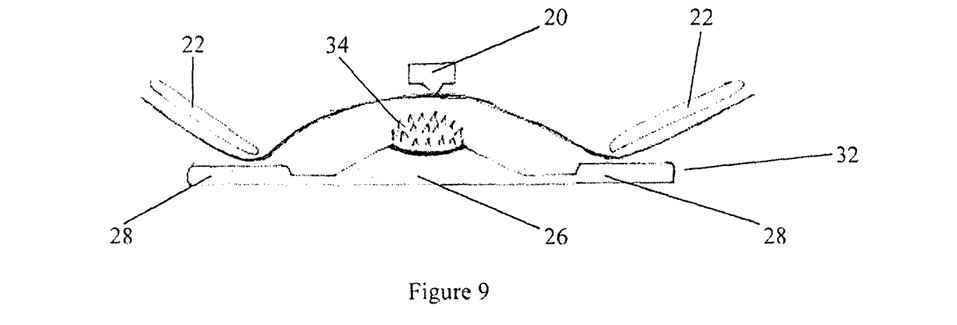
FIG. 9 is a cross-sectional view of the sensory means of an exercise device according to an embodiment of the invention illustrating a flattened thoracic curve and protruding scapula.

A cross-sectional view of the sensory means 32 of an exercise device illustrating a flattened thoracic curve is shown in FIG. 9. The weakened thoracic curve has flattened 20 (as depicted in FIG. 4) and cannot be felt by the wearer against the spine contact member 26 and associated protrusions 34. However, the rigid planar members 28 can be felt on top of the shoulder blades 22, which are in a 'winging' position.

Referring generally to FIGS. 7, 8 and 9, the use of the exercise device to strengthen the scapula-thoracic region and specifically facilitate and strengthen the serratus anterior in its weight-bearing role is dependent on the height 36 of the spine contact member 26 and associated protrusions 34. It is the sensory feedback of the spine contact member 26 and associated protrusions 34 to the wearer when postural form is good (as in FIG. 8), encouraging the wearer to push backwards to form the apex of the thoracic curve and so activate the serratus anterior in its weight-bearing role. This correct muscle action results in increased pressure under the spine contact member 26 and associated protrusions 34 and decreased pressure under the rigid planar members 28 as the scapulae flatten against the chest wall.

Figure 10A:
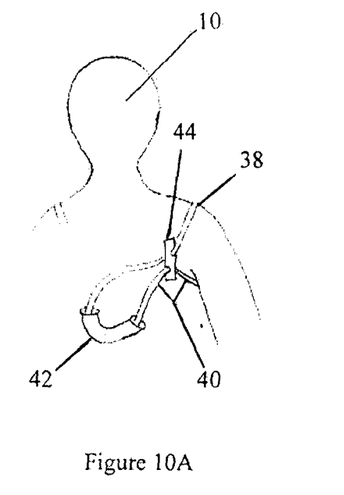
FIG. 10A illustrates a front view showing an adjustable strap system about one shoulder.

FIG. 10A illustrates a front view of an adjustable strap system about one shoulder. The portion of the adjustable strap system shown comprises a shoulder elastic exercise band 38, an underarm elastic exercise band 40, a movable hand-grip 42 and a cleat 44. The shoulder elastic exercise band 38 meets the underarm elastic exercise band 40 in the front of a wearer 10 of the device as a continuous band. The cleat 44 enables the elastic exercise bands 38 and 40 to be adjusted to suit the size of the wearer. The movable hand-grip 42 enables a user to easily grip the exercise band during exercise.

Figure 10B:
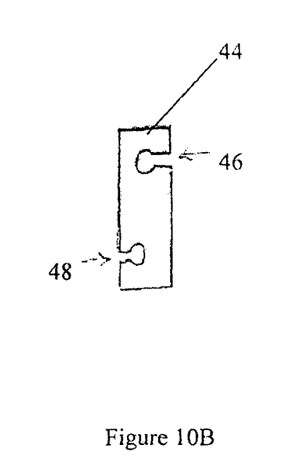
FIG. 10B is an enlarged view of a cleat used for adjustment of the strap system.

FIG. 10B is an enlarged view of the cleat 44 shown in FIG. 10A. The cleat 44 has a top opening 46 and a bottom opening 48 for engaging and holding an elastic exercise band (not shown).

During use, the spine contact member and rigid planar members are positioned against the back of a user, with the spine contact member positioned on the thoracic curve of the wearer and each rigid planar member positioned over a scapula of the wearer. The elastic exercise bands are passed over and under each shoulder and a cleat positioned vertically at the front of each shoulder to hold the device firmly in position. If the spine contact member and rigid planar members are not correctly positioned, the cleat position on the elastic exercise bands can be adjusted until the spine contact member and rigid planar members are correctly positioned.

Performing a pushing, simulated weight-bearing action of the upper limb with the elastic exercise bands, combined with a push back action against the spine contact member on the apex of the thoracic spine, while maintaining good postural form, allows the correct recruitment of serratus anterior and also axial compression through the entire upper limb and scapula-thoracic region to strengthen this region of the spine.

Figure 11:
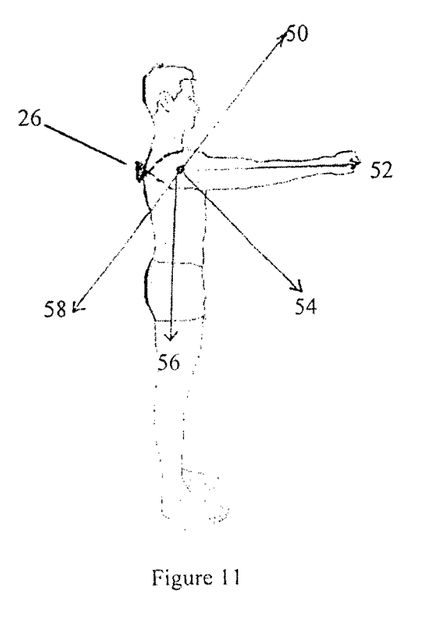

FIG. 11 is a side view of a person wearing an exercise device of the invention and shows some of the different directions, 50, 52, 54, 56 and 58 that the combination of movable hand-grips and cleats allows pushing exercises to be undertaken in.

Figure 12:
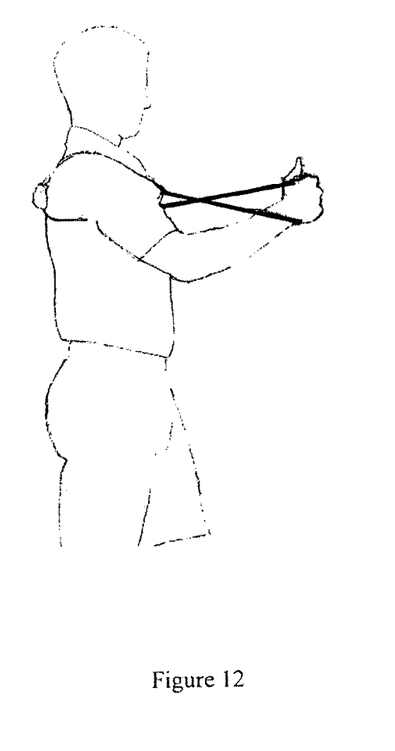
FIG. 12 is a side view of a person wearing an exercise device of the invention, undertaking a pushing out exercise (position 52 of FIG. 10) combined with axial compression and axial external rotation of the upper limb.

Exercise devices according to the invention also allow exercises to be performed in various positions of axial rotation of the upper limb combined with simulated weight-bearing (axial compression). FIG. 12 illustrates activation of the thoracic curve combined with a pushing out exercise (position 52 of FIG. 10) combined with axial compression and axial external rotation of the upper limb.

Figure 13:
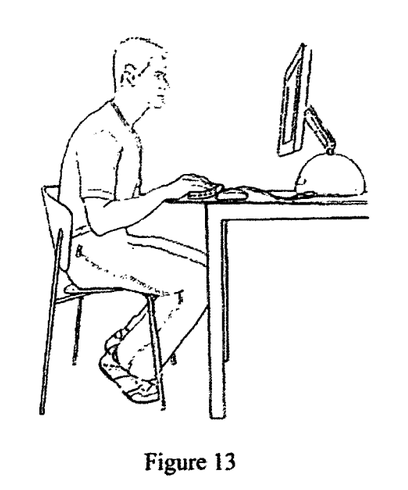
FIG. 13 is a depiction of poor, slumped posture.
Figure 14:
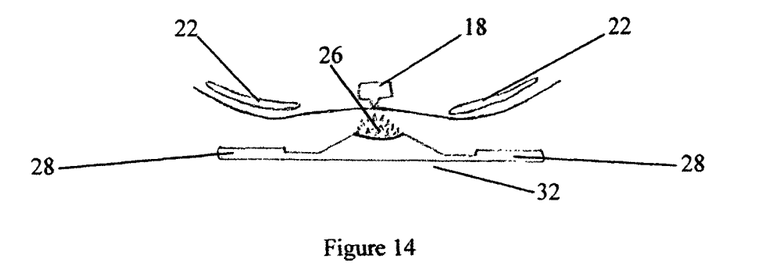
FIG. 14 is a cross-sectional view of the sensory means of an exercise device according to an embodiment of the invention on a person with poor, slumped posture.

Poor, slumped posture is depicted in FIG. 13. FIG. 14 is a cross-sectional view of the sensory means 32 of an exercise device according to an embodiment of the invention on a person with poor, slumped posture. The shoulders and scapula 22 have moved forward and are no longer in contact with the rigid planar members 28. In addition, there is a marked increase in pressure of the spine contact member 26 against the thoracic region of the spine 18.

Figure 15:
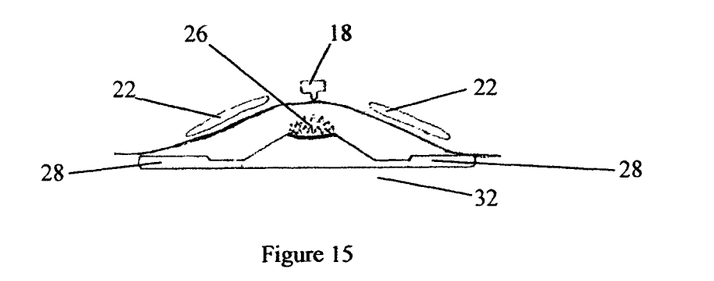
FIG. 15 is a cross-sectional view of the sensory means of an exercise device according to an embodiment of the invention on a person with poor posture where the spine is arched backwards.

FIG. 15 is a cross-sectional view of the sensory means 32 of an exercise device according to an embodiment of the invention on a person with poor posture where the spine is arched backwards (as during exercise in FIG. 3). The shoulders and scapula 22 are in contact with the rigid planar members 28 and there is a marked reduction in pressure of the spine contact member 26 against the thoracic curve of the spine 18.

An exercise device according to the invention can be used simply as a postural feedback device to correct the poor postures illustrated in FIGS. 14 and 15. That is, the exercise device is not limited to use during weight-bearing exercises of the upper limbs. During daily activities and exercises, the exercise device provides feedback on the position of the apex of the thoracic spine in relation to the position of the shoulder blades and can thus assist in maintaining good posture (as illustrated in FIG. 8).

Figure 16:
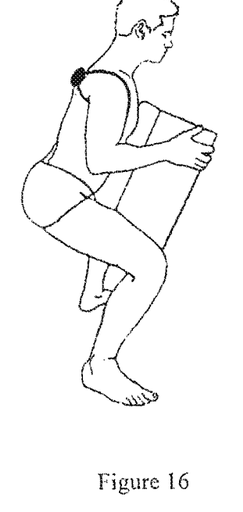
FIG. 16 is a depiction of a person wearing an exercise device according to an embodiment of the invention to assist with maintaining good posture during lifting.
Figure 17:
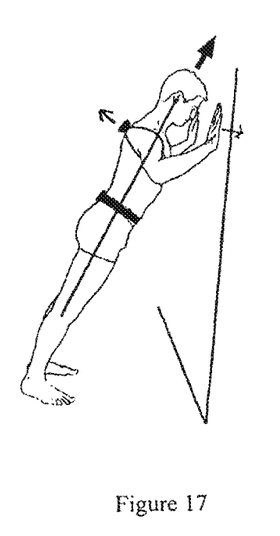
FIG. 17 is a depiction of a person wearing an exercise device according to an embodiment of the invention to assist with maintaining good posture during push-up exercises against a wall.

For example, an exercise device according to the invention can be used to provide feedback on posture whilst using the upper limbs in functional activities such as lifting (illustrated in FIG. 16) or during exercises such as push-up exercises against a wall (illustrated in FIG. 17).

Figure 18:
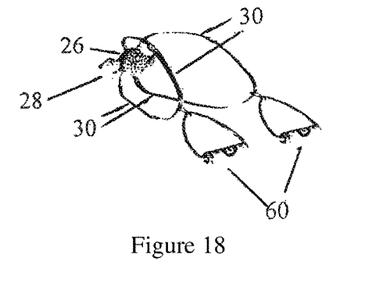
FIG. 18 shows an exercise device according to an alternative embodiment of the invention.

In FIG. 18 there is shown an exercise device 24 according to an alternative embodiment of the invention. The device 24 comprises a spine contact member 26 to be positioned at the thoracic curve of a person wearing the device, and two rigid planar members 28 which extend laterally from the spine contact member 26. The rigid planar members 28 are positioned over the scapulae of the wearer. The spine contact member 26 and associated rigid planar members 28 are held in position by adjustable straps 30 which pass over and under the shoulders of the wearer.

The device 24 further comprises separate handles 60. The handles 60 slide on the adjustable straps 30 to allow a 'push out' exercise against the adjustable straps 30 in multidirectional simulated weight-bearing exercise for the upper limb. The handles 60 are detachable from the adjustable straps 30 allowing the exercise device to be readily used as a posture feedback device.

It can thus be seen that an exercise device of the present invention provides an external sensory feedback device for facilitation and strengthening of the scapulo-thoracic region, particularly the serratus anterior, during exercise. An exercise device of the present invention can also be used to provide feedback on postural awareness and monitor good postural form during daily activities and exercises.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention, is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. An exercise device comprising:
   (i) sensory means comprising a spine contact member and two rigid planar members extending laterally from the spine contact member; and
   (ii) an adjustable strap system for securing the sensory means to a wearer of said exercise device, wherein said adjustable strap system comprises at least one flexible, extensible strap;
   wherein the spine contact member is convexly shaped, thereby having an apex, and protrudes from a plane defined by the two rigid planar members, such that in use, the apex of the spine contact member is positioned on an apex of a thoracic curve of the wearer and presses onto the thoracic curve, thereby providing tactile feedback, and each of the rigid planar members is positioned over a scapula of the wearer.

2. The exercise device of claim 1, wherein the at least one flexible extensible, strap is an elastic resistant band.

3. The exercise device of claim 2, wherein the at least one flexible extensible, strap comprises two flexible, extensible straps, wherein said two flexible, extensible straps are elastic resistant bands.

4. The exercise device of claim 3, wherein the adjustable strap system comprises gripping means adapted to be gripped by hands of the wearer during exercises.

5. The exercise device of claim 4, wherein the gripping means are integrally formed with each of the two elastic resistant bands, or wherein the gripping means comprise a handle for each hand.

6. The exercise device of claim 3, wherein the adjustable strap system further comprises two devices, each of the two devices being associated with one of the two elastic resistant bands for adjusting a length of the respective elastic resistant band.

7. The exercise device of claim 2, wherein the adjustable strap system comprises gripping means adapted to be gripped by hands of the wearer during exercises.

8. The exercise device of claim 7, wherein the gripping means are integrally formed with the at least one elastic resistant band.

9. The exercise device of claim 7, wherein the gripping means comprise a handle for each hand.

10. The exercise device of claim 2, wherein the adjustable strap system further comprises at least one device for adjusting the length of the at least one resistant band.

11. The exercise device of claim 10 wherein the at least one device for adjusting the length of the at least one elastic resistant band is selected from the group consisting of a buckle, clip and cleat.

12. The exercise device of claim 1, wherein the sensory means further comprises at least one pressure sensor.

13. The exercise device of claim 12, wherein the at least one pressure sensor is an electronic pressure sensor.

14. The exercise device of claim 13, wherein the electronic pressure sensor is in wireless communication with a pressure monitoring device.

15. The exercise device of claim 12, wherein the at least one pressure sensor is associated with the spine contact member.

16. The exercise device of claim 12, wherein the at least one pressure sensor comprises two pressure sensors that are associated with the rigid planar members, such that each of the rigid planar members has an associated pressure sensor of the two pressure sensors.

17. The exercise device of claim 12, wherein the at least one pressure sensors comprises three pressure sensors, two of the three pressure sensors are associated with the rigid planar members, such that each of the rigid planar members has an associated pressure sensor of the two pressure sensors, and a third pressure sensor of the three pressure sensors is associated with the spine contact member.

18. The exercise device of claim 1, wherein the spine contact member has a smooth surface that contacts the thoracic curve of the wearer.

19. The exercise device of claim 1, wherein the spine contact member has one or more projections on the surface that contacts the thoracic curve of the wearer.

20. The exercise device of claim 1, wherein the spine contact member and two rigid planar members are separate components.

* * * * *